US012453648B2

(12) United States Patent
Li

(10) Patent No.: US 12,453,648 B2
(45) Date of Patent: Oct. 28, 2025

(54) ADJUSTING DEVICE AND ADJUSTABLE CERVICAL SPINE FIXATOR

(71) Applicant: SHENZHEN AONUO MEDICAL TECHNOLOGY CO., LTD., Guangdong (CN)

(72) Inventor: Zhenyu Li, Guangdong (CN)

(73) Assignee: SHENZHEN AONUO MEDICAL TECHNOLOGY CO., LTD., Guangdong (CN)

( * ) Notice: Subject to any disclaimer, the term of this patent is extended or adjusted under 35 U.S.C. 154(b) by 0 days.

(21) Appl. No.: 18/269,877

(22) PCT Filed: Jan. 19, 2022

(86) PCT No.: PCT/CN2022/072757
§ 371 (c)(1),
(2) Date: Jun. 27, 2023

(87) PCT Pub. No.: WO2023/050658
PCT Pub. Date: Apr. 6, 2023

(65) Prior Publication Data
US 2024/0225883 A1 Jul. 11, 2024

(30) Foreign Application Priority Data
Sep. 30, 2021 (CN) .......................... 202111166967.3

(51) Int. Cl.
*A61F 5/055* (2006.01)

(52) U.S. Cl.
CPC .................................... *A61F 5/055* (2013.01)

(58) Field of Classification Search
CPC .. A61F 5/055; A61F 5/05; A61F 5/048; A61F 5/042; A61F 5/04; A61F 5/05883; A61F 5/3707
See application file for complete search history.

(56) References Cited

FOREIGN PATENT DOCUMENTS

| | | |
|---|---|---|
| CN | 2822564 Y | 10/2006 |
| CN | 202015274 U | 10/2011 |

(Continued)

OTHER PUBLICATIONS

International Search Report dated Apr. 6, 2023; International Application No. PCT/CN2022/072757; 5 pages (non-English).

(Continued)

*Primary Examiner* — Tarla R Patel
(74) *Attorney, Agent, or Firm* — CANTOR COLBURN LLP

(57) ABSTRACT

An adjusting device, including: a rotating structure, including a connection member having one end being connected with the target and another end rotatable; and a positioning structure, including a locking member and a positioning member matching with the locking member. The locking member is arranged at a rotatable end of the connection member along a rotation direction of the connection member, one end of the positioning member is slidably arranged relative to the locking member, and another end of the positioning member is fixedly arranged. The connection member is configured to rotate in a predetermined direction, and drive a slidable end of the positioning member to slide in a direction away from the locking member. The slidable end of the positioning member is configured to reset and engage with the locking member and reversely restrict rotation of the connection member, after the connection member is rotated in place.

19 Claims, 9 Drawing Sheets

(56) References Cited

FOREIGN PATENT DOCUMENTS

| | | | | | |
|---|---|---|---|---|---|
| CN | 202365978 | U | | 8/2012 | |
| CN | 206304012 | U | | 7/2017 | |
| CN | 206526153 | U | | 9/2017 | |
| CN | 109620507 | A | | 4/2019 | |
| CN | 109806051 | A | | 5/2019 | |
| CN | 211271474 | U | | 8/2020 | |
| CN | 111773032 | A | | 10/2020 | |
| CN | 111803260 | A | | 10/2020 | |
| CN | 112155822 | A | | 1/2021 | |
| CN | 112294517 | A | * | 2/2021 | ............. A61F 5/055 |
| CN | 213047545 | U | | 4/2021 | |
| CN | 113730066 | A | * | 12/2021 | ........... A61F 5/0104 |
| CN | 113855363 | A | | 12/2021 | |
| CN | 113905693 | A | * | 1/2022 | ............... A61F 5/05 |
| CN | 115040307 | A | * | 9/2022 | ............. A61F 5/055 |
| CN | 116889489 | A | * | 10/2023 | ............. A61F 5/055 |
| DE | 202018100997 | U1 | * | 5/2019 | ............. A61F 5/055 |
| EP | 3530241 | A1 | | 8/2019 | |

OTHER PUBLICATIONS

International Search Report dated Apr. 6, 2023; International Application No. PCT/CN2022/072757; 3 pages (English).

Written Opinion dated Apr. 6, 2023; International Application No. PCT/CN2022/072757; 5 pages (non-English).

* cited by examiner

ADJUSTING DEVICE AND ADJUSTABLE CERVICAL SPINE FIXATOR

CROSS-REFERENCE TO RELATED APPLICATIONS

This application is the U.S. national phase of International Application No. PCT/CN2022/072757 with an international filing date of Jan. 19, 2022, designating the U.S., now pending, and claims the priority of Chinese patent application number 202111166967.3 filed with the China Patent Office on Sep. 30, 2021 and titled "ADJUSTING DEVICE AND ADJUSTABLE CERVICAL SPINE FIXATOR", the entire contents each of which are incorporated in this application by reference.

TECHNICAL FIELD

The present application relates to the field of medical equipment technical equipment, and more particularly to an adjusting device and an adjustable cervical spine fixator.

BACKGROUND

The statements herein merely provide background information related to the present application and may not necessarily constitute prior art.

Cervical spine is an important part of the human spine. Due to the characteristics of the physiological structure and the needs of physiological activities, this part is most vulnerable to damage, especially for people over 40 years old and those who work at desks for a long time. The age of onset of the cervical spondylosis tends to be younger year by year, and the incidence is high. Science has shown that most cervical spondylosis can be cured through non-surgical treatment, such as cervical traction therapy, which has become the main method of non-surgical treatment of cervical spondylosis, has been recognized by the industry, and is widely used at home and abroad.

Conventional products of this type are generally provided with a mandibular support to support the lower jaw of human body through the mandibular support. Generally, the mandibular support is moved upward toward the lower jaw of the human body to realize effective support of the lower jaw. Usually the mandibular support is rotated by a button or adjusted by a long rack to realize the movement toward the lower jaw of the human body.

However, the rotation operation by the button requires a large operating torque; and the adjustment of the rack for raising the mandibular support is also laborious and noisy.

SUMMARY

It is one of objectives of embodiments of the present application to provide an adjusting device, which aims at solving the problem of how to simplify the process of adjusting the elevation of the mandibular support.

In order to solve the above technical problems, the following technical solutions are adopted by embodiments of the present application:

In a first aspect, an adjusting device is provided. The adjusting device is configured to adjust a position of a target. The adjusting device comprises:

- a rotating structure, comprising a connection member, in which, one end of the connection member is connected with the target and another end of the connection member is rotatable; and
- a positioning structure, comprising a locking member and a positioning member matching with the locking member; in which, the locking member is arranged at a rotatable end of the connection member along a rotation direction of the connection member, one end of the positioning member is slidably arranged relative to the locking member, and another end of the positioning member is fixedly arranged.

The connection member is configured to rotate in a predetermined direction, and drive a slidable end of the positioning member to slide in a direction away from the locking member. The slidable end of the positioning member is configured to reset and engage with the locking member and reversely restrict rotation of the connection member, after the connection member is rotated in place.

In some embodiments, the locking member comprises ratchet teeth, and the ratchet teeth are arranged at intervals along a peripheral side of the connection member, and a positioning groove is formed between any two adjacent ratchet teeth, and one end of the positioning member is engaged into one positioning groove.

In some embodiments, the connection member comprises a connection body and a wheel body connected to the connection body; and the ratchet teeth are arranged at a peripheral side of the wheel body.

In some embodiments, the connection body defines therein a connection hole, a cross-section of the connection hole has a non-circular shape, and the wheel body protrudes towards the connection hole to form a connection portion.

In some embodiments, a guide column is arranged in the connection hole, and a guide hole matching with the guide column is defined in a position of the connection portion corresponding to the guide column. One end of the guide column is plugged into the guide hole.

In some embodiments, each of the ratchet teeth is arranged obliquely, and an inclination direction of each of the ratchet teeth is opposite to the predetermined direction.

In some embodiments, the positioning member comprises: a tongue fitting with the locking member, and a reset member having an elastic restoration. The tongue is slidably arranged relative to the locking member and in connection with one end of the reset member, and another end of the reset member is fixedly arranged.

In some embodiments, the adjusting device further comprises an unlocking structure, and the unlocking structure comprises a pull cord, one end of the pull cord is connected to the tongue.

In some embodiments, the adjusting device further comprises a cowl casing having an accommodation chamber. An avoidance hole in communication with the accommodation chamber is defined in surface of the cowl casing. One end of the connection member is inserted into the accommodation chamber via the avoidance hole and is rotatably connected to a wall of the accommodation chamber. The positioning structure and the pull cord are both located in the accommodation chamber.

In some embodiments, a guide slot is arranged in the accommodation chamber. One end of the guide slot extends to a connection end of the connection member, and the reset member is arranged on another end of the guide slot. The tongue comprises: a tongue tip matching with the locking member, a guide block connected with the tongue tip, and a positioning column connected with the guide block and the reset member. The pull cord is connected to the positioning column.

In an embodiment, an end of the guide block abutting against the reset member defines therein a limiting groove, and the positioning column is connected to a bottom of the limiting groove. The reset member is a tube spring, and the tube spring is sleeved outside the positioning column. One end of the tube spring abuts against the bottom of the limiting groove, and another end of the tube spring abuts against an inner wall of the guide slot.

In an embodiment, the inner wall of the guide slot defines therein an avoidance groove, and one end of the positioning column is protruded out of the guide slot via the avoidance groove and connected with the pull cord.

In an embodiment, two rotating structures are provided. The two rotating structures are respectively located at two ends of the cowl casing. A number of positioning structures is equivalent to that of the rotating structures, and the positioning structures and the rotating structures are arranged one-to-one correspondence. The pull cord is arranged along an inner wall of the accommodation chamber, and two ends of the pull cord are respectively connected to two tongues.

In an embodiment, the cowl casing further defines therein an unlocking hole communicating with the accommodation chamber. The unlocking structure further comprises: an unlocking button, which is located in the unlocking hole and has one end of the unlocking button connected to the pull cord, and rollers, which are arranged in the accommodation chamber and configured to guide the pull cord to shrink.

In an embodiment, a roller surface of each of the rollers defines a positioning circular groove, and the pull cord is partially accommodated in the positioning circular groove.

In a second aspect, it is another objective of the present application to provide an adjustable cervical spine fixator, which includes the adjusting device as described in the above.

Advantages of the adjusting device according to embodiments of the present application are summarized as follows: when a height of the mandibular support needs to be raised, an external force directly drives the mandibular support to rotate upwards, and the locking member pushes the slidable end of the positioning member to slide outward. After the external force is removed, the slidable end of the positioning member resets and engages with the locking member, and the locking member reversely engages with the slidable end of the positioning member, so as to realize the positioning of the mandibular support. The operation process is simple and efficient.

BRIEF DESCRIPTION OF THE DRAWINGS

In order to more clearly illustrate the technical solutions in the embodiments of the present application, the drawings that need to be used in the description of the embodiments or the prior art will be briefly described hereinbelow. Obviously, the accompanying drawings in the following description are only some embodiments of the present application. For those skilled in the art, other drawings can be obtained based on these drawings without creative work.

DETAILED DESCRIPTION OF THE DRAWINGS

Figure 1:
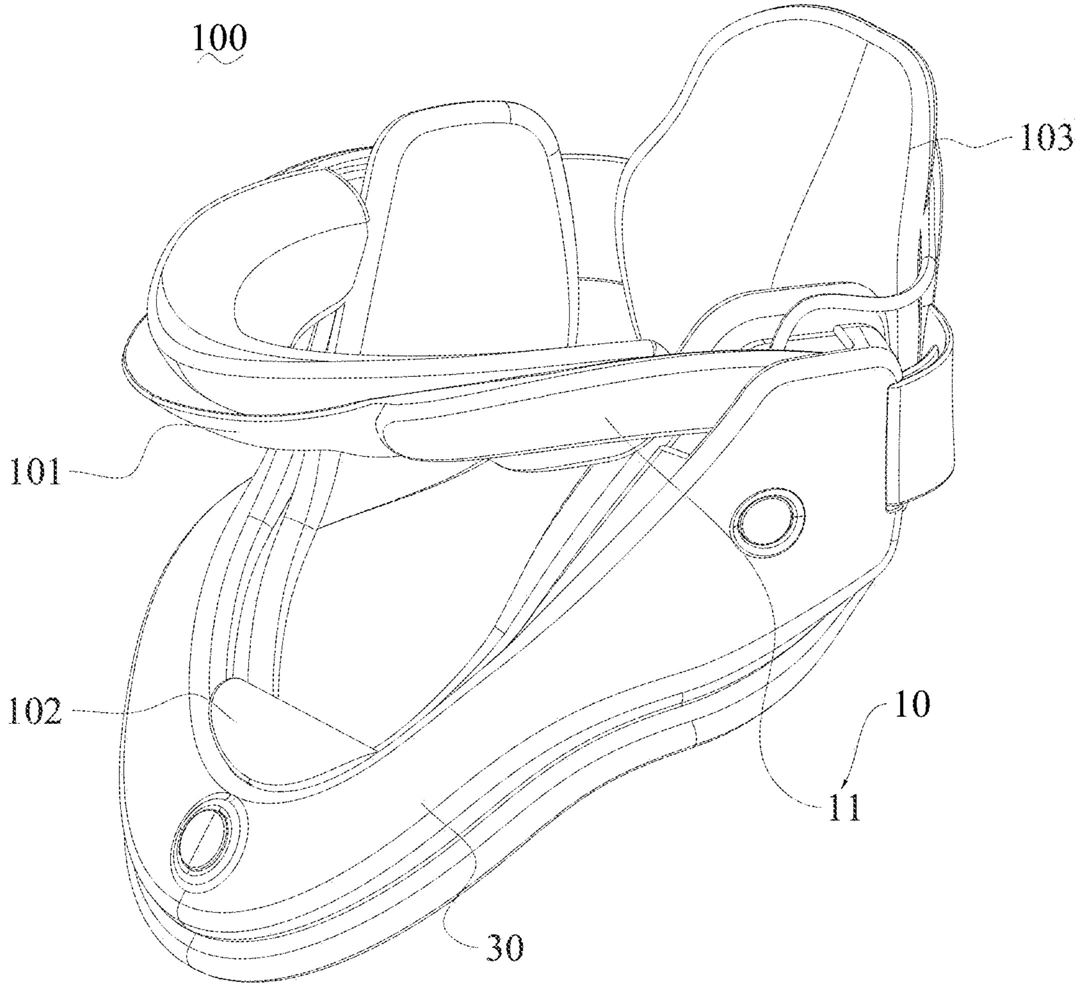
FIG. 1 is a perspective structural schematic diagram of an adjusting device provided in an embodiment of the present application.
Figure 2:
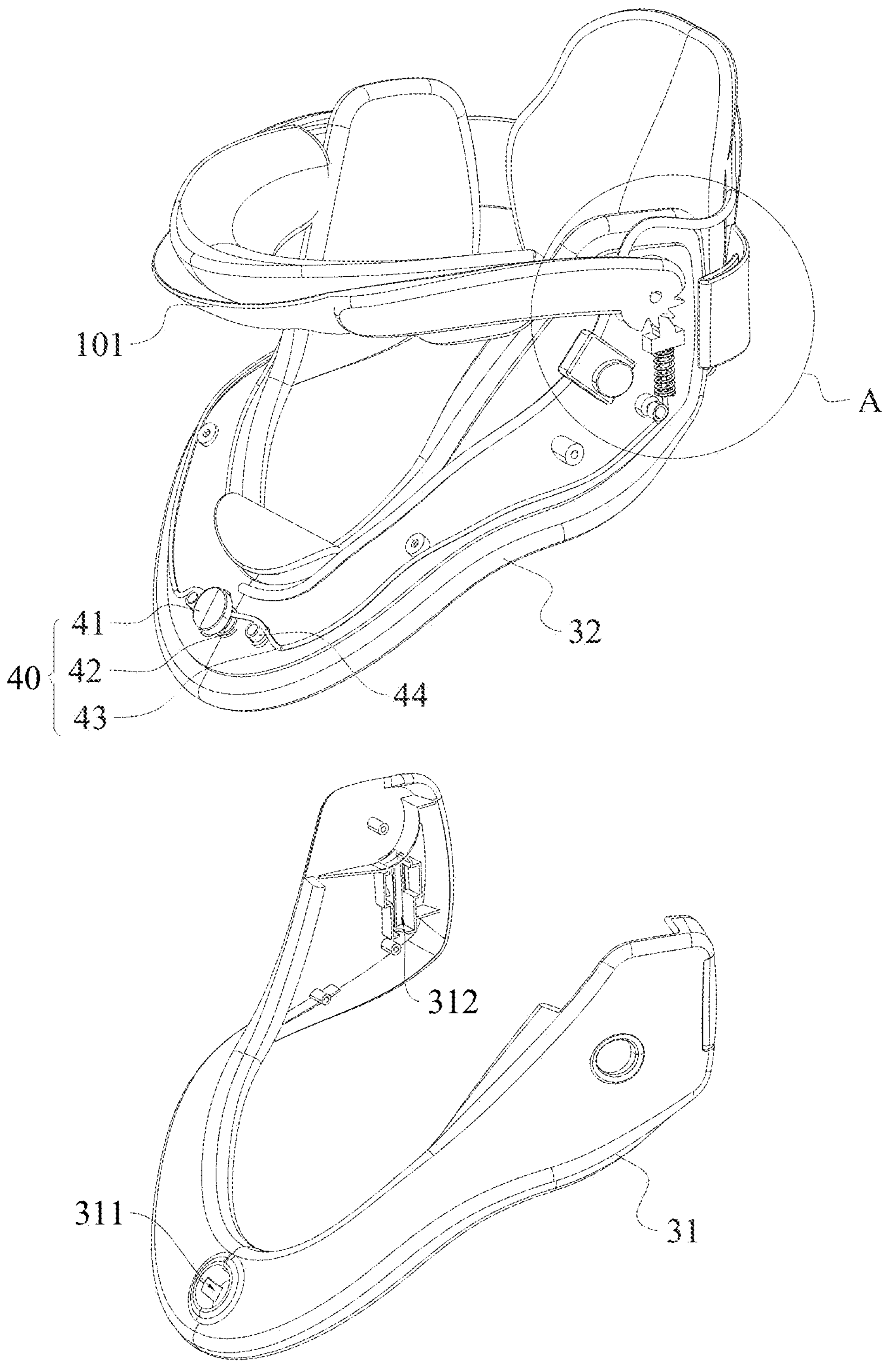
FIG. 2 is an exploded schematic diagram of the adjusting device of FIG. 1.

In order to make the purposes, technical solutions, and advantages of the present application clearer and more understandable, the present application will be further described in detail hereinafter with reference to the accompanying drawings and embodiments. It should be understood that the embodiments described herein are only intended to illustrate but not to limit the present application.

It should be noted that when an element is described as "fixed" or "arranged" on/at another element, it means that the element can be directly or indirectly fixed or arranged on/at another element. When an element is described as "connected" to/with another element, it means that the element can be directly or indirectly connected to/with another element. The orientation or positional relationship indicated by the terms "upper", "lower", "left", "right", and the like is based on the orientation or positional relationship shown in the drawings, and is only for the convenience of description, rather than indicating or implying the referred device or element must have a specific orientation, be constructed and operated in a specific orientation, and therefore should not be construed as a limitation on the present application, and those of ordinary skill in the art can understand the specific meanings of the above terms according to specific situations. Terms like "first" and "second" are only used for the purpose of description, and will in no way be interpreted as indication or hint of relative importance or implicitly indicate the number of the referred technical features. In the description of the present application, "multiple"/"a plurality of" refers to the number of two or more than two, unless otherwise clearly and specifically defined.

Figure 3:
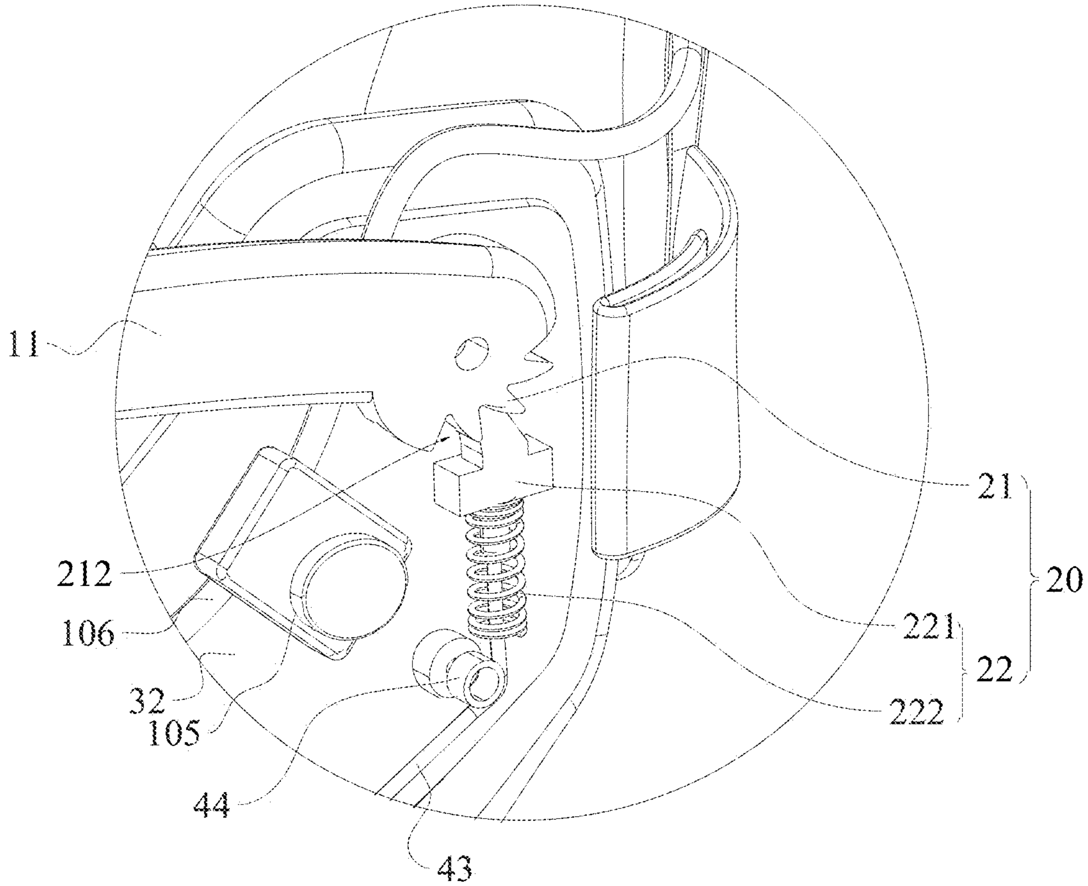
FIG. 3 is a partial enlarged view of Part A taken from FIG. 2.

Referring to FIG. 1 and FIG. 3, embodiments of the present application provides an adjusting device 100 configured to adjust a position of an object.

Optionally, in this embodiment, the target object is a mandibular support 101, and the adjusting device 100 can rotate the mandibular support 101 and meanwhile raise a height of the mandibular support 101, so that the mandibular support 101 abuts against a lower jaw of a human body, thereby realizing an effective support for the lower jaw. Optionally, the mandibular support 101 is configured in an arc shape and is to be arranged around a circumference of the lower jaw of the human body.

The adjusting device 100 comprises: a rotating structure 10 and a positioning structure 20. The rotating structure 10 comprises a connection member 11. The connection member 11 has one end connected to the target and the other end of the connection member 11 is rotatable. Optionally, the mandibular support 101 is connected to one end of the connection member 11, and rotates along with the rotation of the connection member 11. In this embodiment, the connection member 11 drives the mandibular support to move upward, so that the mandibular support abuts against the lower jaw of the human body.

Referring to FIG. 1 and FIG. 3, the positioning structure 20 includes a locking member 21 and a positioning member 22 matching with the locking member 21, and the locking member 21 is arranged at a rotatable end of the connection member 11 along a rotation direction of the connection member 11. One end of the positioning member 22 is slidably arranged relative to the locking member 21, and the other end of the positioning member 22 is fixedly arranged. Optionally, the slidable end of the positioning member 22 can slide to and abut against the locking member 21.

The connection member 11 is configured to rotate in a predetermined direction, and drive the slidable end of the positioning member 22 to slide in a direction away from the locking member 21. In this embodiment, the predetermined direction is to make the mandibular support 101 rotate upward. After the connection member 11 is rotated in place, the slidable end of the positioning member 22 resets and engages with the locking member 21, and reversely restricts rotation of the connection member 11. It can be understood that the slidable end of the positioning member 22 is configured to reversely engage with the locking member 21 after the connection member 11 is rotated in place, so as to reversely limit the rotation of the connection member 11. That is, the slidable end of the positioning member 22 does not restrict the upward rotation of the connection member 11, but restricts the downward rotation of the connection member 11.

Referring to FIG. 1 and FIG. 3, when a height of the mandibular support 101 needs to be raised, an external force directly drives the mandibular support 101 to rotate upwards, and the locking member 21 pushes the slidable end of the positioning member 22 to slide outward. After the external force is removed, the slidable end of the positioning member 22 resets and engages with the locking member 21, and the locking member 21 reversely engages with the slidable end of the positioning member 22, so as to realize the positioning of the mandibular support 101. The operation process is simple and efficient.

It can be understood that, when the connection member 11 is in a static state, under the action of gravity of the connection member 11, the locking member 21 and the slidable end of the positioning member 22 are reversely engaged, thereby restricting the downward rotation of the connection member 11, and enabling the mandibular support 101 to effectively support the lower jaw of the human body.

Referring to FIGS. 1 and 3, it can be understood that under the action of an external force, the slidable end of the drive positioning member 22 is driven to slide in a direction away from the locking member 21, to enable the positioning member 22 to disengage from the locking member 21, so that the positioning member 22 releases the rotation restriction on the connection member 11, and the connection member 11 can rotate downwards to adjust the position of the mandibular support 101.

Figure 4:
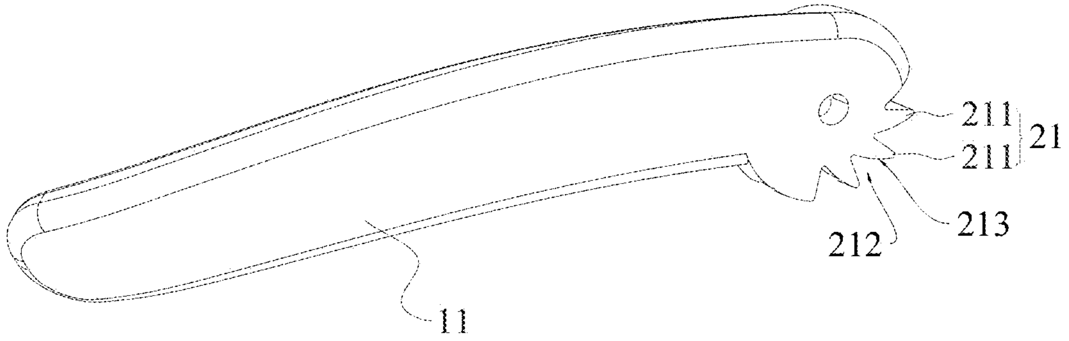
FIG. 4 is a perspective structural schematic diagram of a connection member in FIG. 2.
Figure 6:
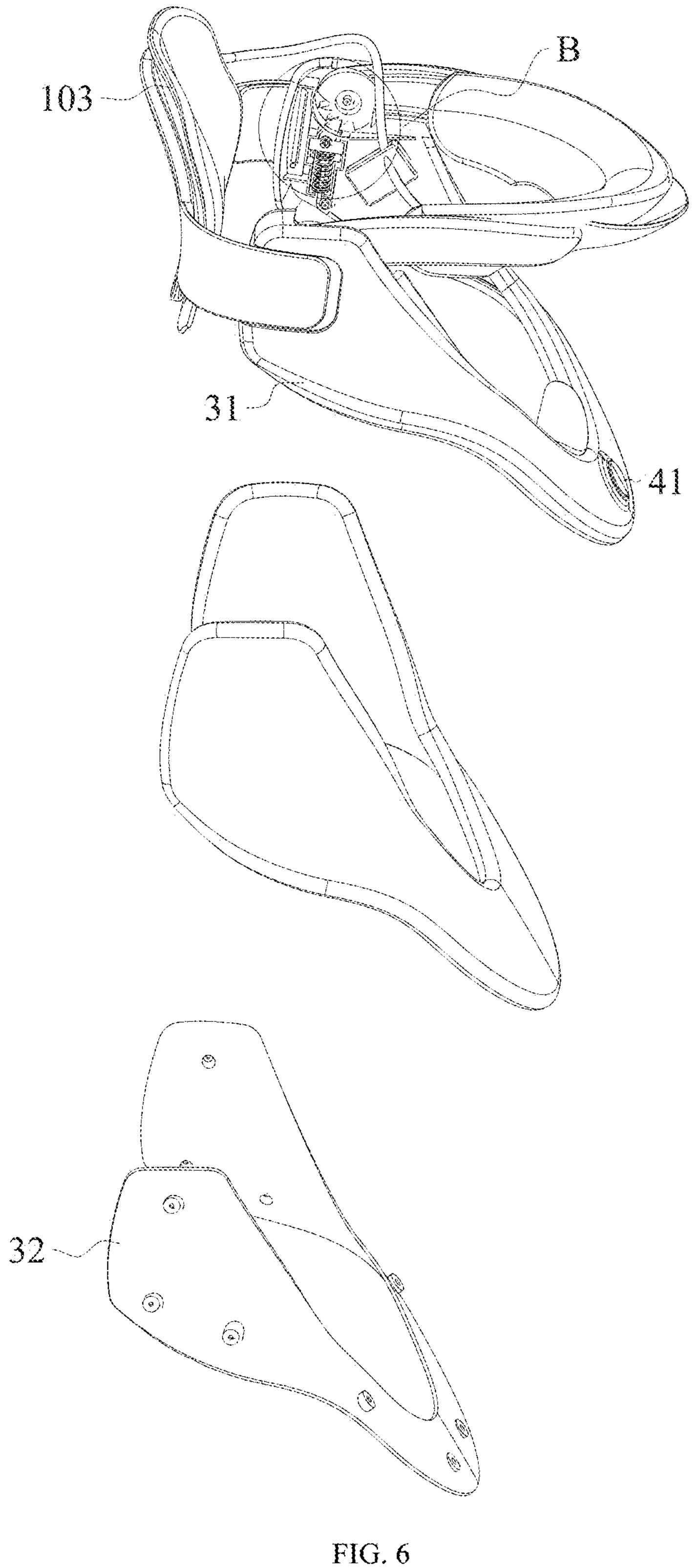
FIG. 6 is a further exploded schematic diagram of the adjusting device of FIG. 2.

Referring to FIG. 4 and FIG. 6, in an embodiment, the locking member 21 includes ratchet teeth 211, and the ratchet teeth 211 are arranged at intervals along a peripheral side of the connection member 11, and a positioning groove 212 is formed between any two adjacent ratchet teeth 211, and one end of the positioning member 22 is engaged into one of the positioning grooves 212.

Figure 8:
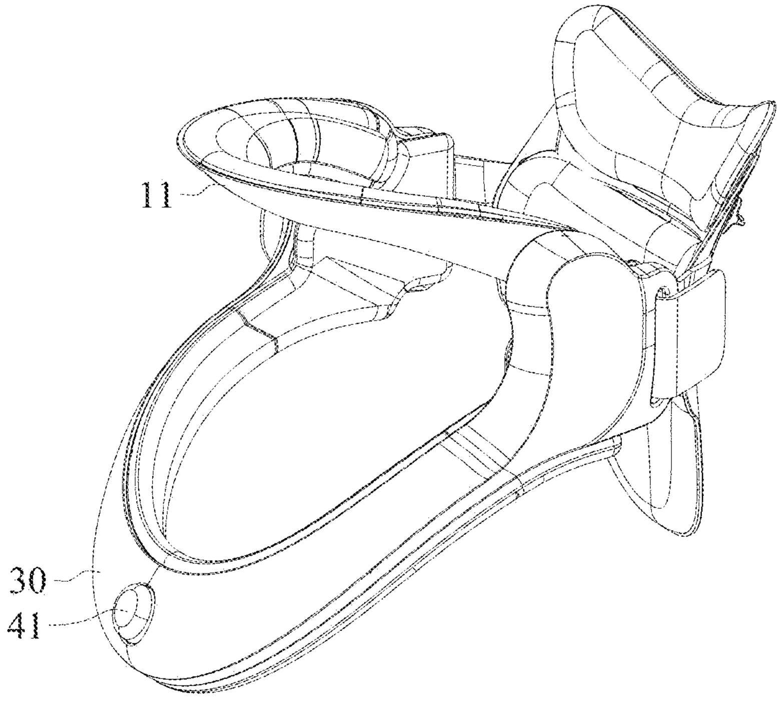
FIG. 8 is a perspective structural schematic diagram of an adjusting device provided by another embodiment of the present application.
Figure 10:
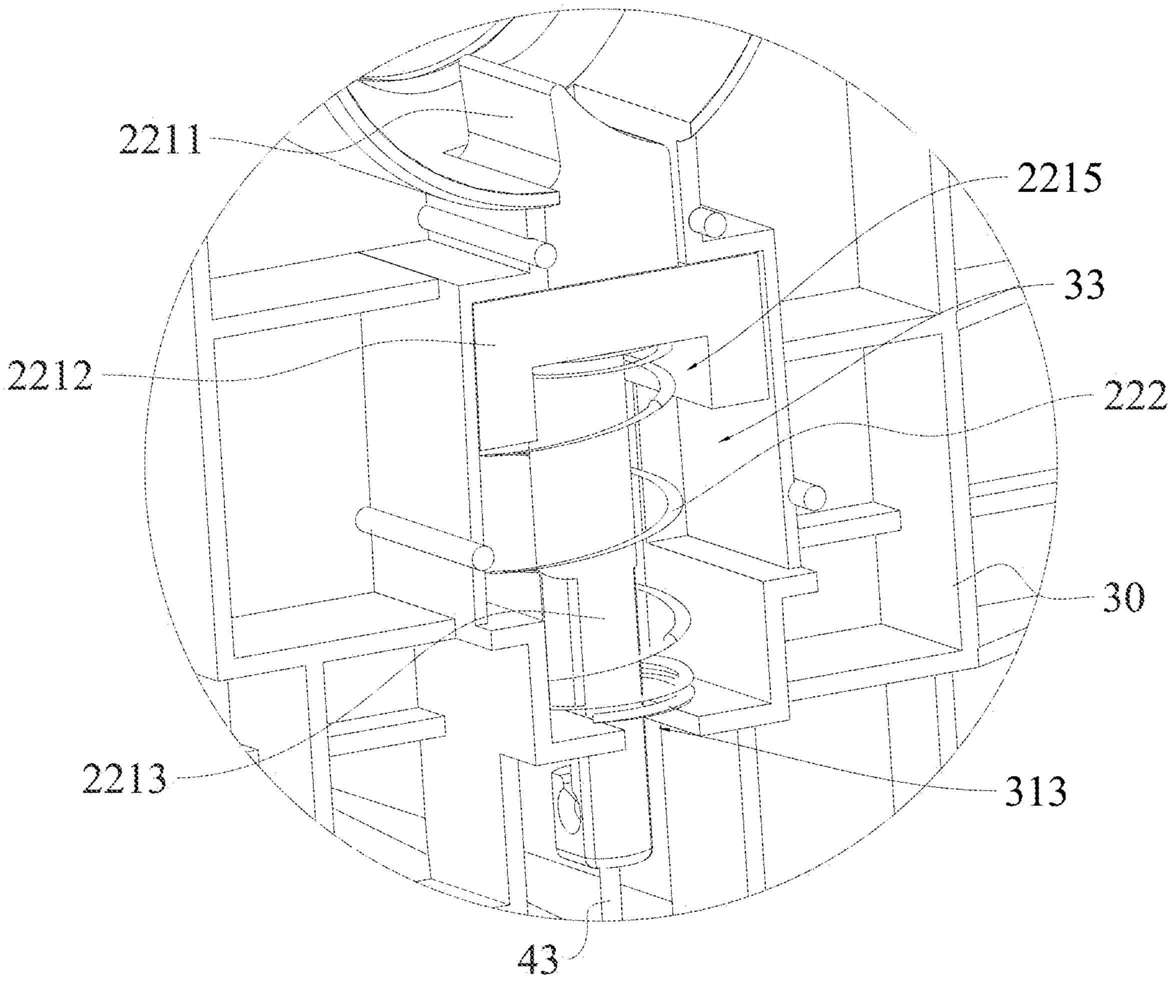
FIG. 10 is a partial enlarged view of Part C taken from FIG. 9.

Referring to FIG. 8 and FIG. 10, in an embodiment, the connection member 11 includes a connection body 111 and a wheel body 112 connected to the connection body 111, and the ratchet teeth 211 are arranged at a peripheral side of the wheel body 112.

Optionally, the mandibular support 101 and the connection body 111 are integrally formed.

Referring to FIG. 8 and FIG. 10, optionally, the ratchet teeth 211 are defined on the peripheral side of the wheel body 112, and the wheel body 112 rotates together with the connection body 111, thereby driving the ratchet teeth 211 to rotate.

Optionally, the connection body 111 is shaped like a crescent or an arc, and the wheel body 112 is connected to an end of the connection body 111.

Referring to FIG. 8 and FIG. 10, it can be understood that the wheel body 112 can be integrally formed with the connection body 111, and optionally, both the wheel body 112 and the connection body 111 are made of plastic materials, so that the wheel body 112 and the connection body 111 can be integrally formed by injection molding.

Referring to FIG. 8 and FIG. 10, it can be understood that the wheel body 112 can also be detachably connected to the connection body 111. Optionally, the wheel body 112 can be detachably connected to the connection body 111 through a thread structure or a snap-fit structure, which facilitates the disassembly between the wheel body 112 and the connection body 111.

Figure 11:
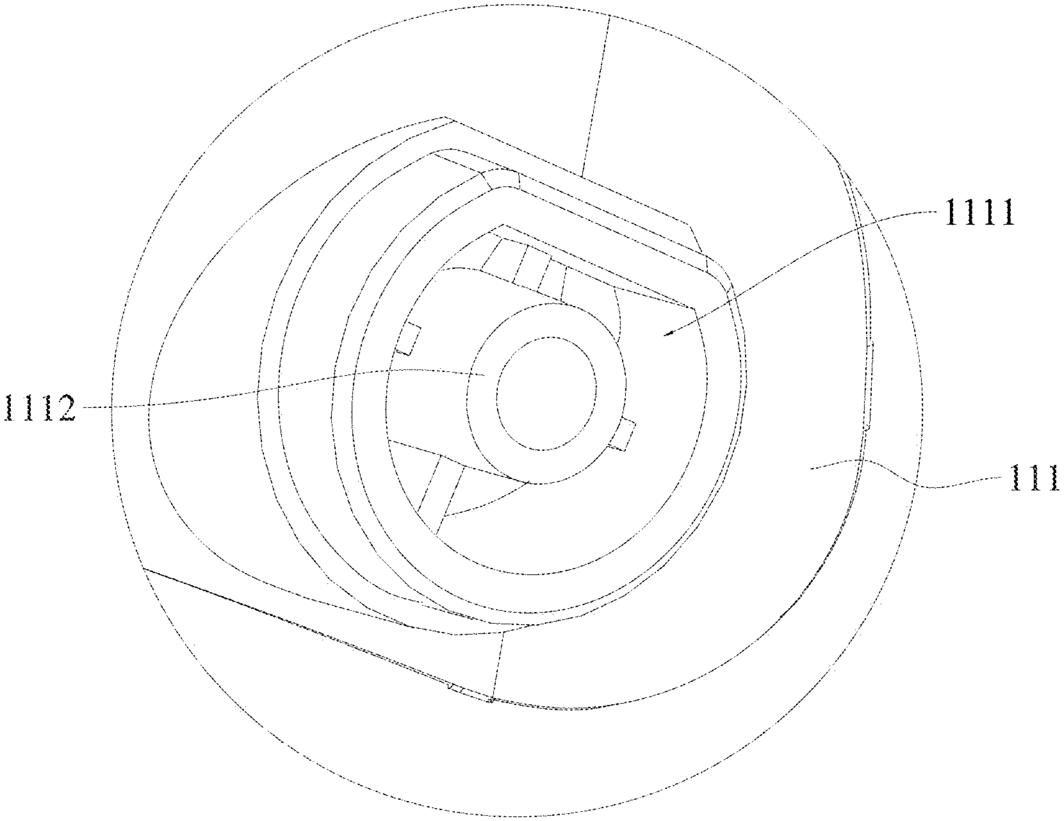
FIG. 11 is a partial enlarged view of Part D taken from FIG. 9.
Figure 12:
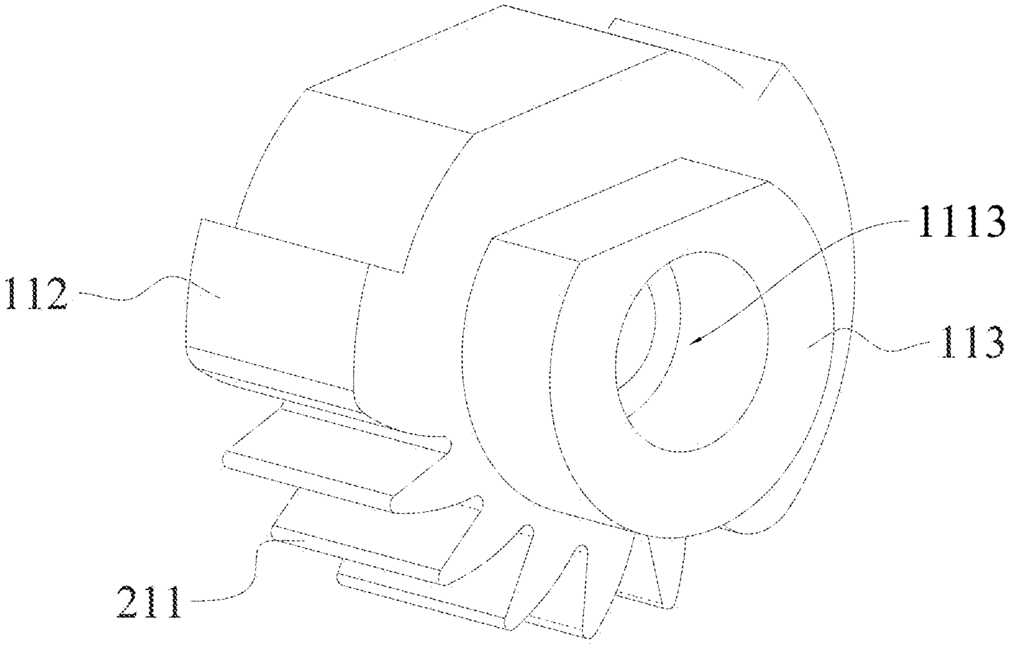
FIG. 12 is a perspective structural schematic diagram of a wheel body in FIG. 9.

Referring to FIG. 11 and FIG. 12, in an embodiment, the connection body 111 defines therein a connection hole 1111, a cross-section of the connection hole 1111 has a non-circular shape, and the wheel body 112 protrudes towards the connection hole 1111 to form a connection portion.

Referring to FIG. 11 and FIG. 12, optionally, a cross-section of the connection hole 1111 has a square, an ellipse, or a special shape.

Referring to FIG. 11 and FIG. 12, in this embodiment, the connection hole 1111 is configured as a flat hole, that is, the cross-section of the connection hole is D-shaped, and the shape of the connection portion 113 matches with the shape of the connection hole 1111. After the connection portion 113 is inserted into the connection hole 1111, since no relative rotation between the D-shaped connection hole 1111 and the connection portion 113 would occur, the wheel body 112 and the connection body 111 can rotate synchronously.

Referring to FIG. 11 and FIG. 12, because both the connection hole 1111 and the connection portion 113 are D-shaped, the connection portion 113 is oriented after being inserted into the connection hole 1111, such that the fitting between the connection hole 1111 and the connection portion 113 may guide the assembly of the wheel body 112 and the connection body 111, and the reliability is high.

Referring to FIG. 11 and FIG. 12, in an embodiment, a guide column 1112 is arranged in the connection hole 1111, and a guide hole 1113 matching with the guide column 1112 is defined in a position of the connection portion corresponding to the guide column 1112. One end of the guide column 1112 is plugged into the guide hole 1113.

Referring to FIG. 11 and FIG. 12, optionally, a cross-section of the guide column 1112 can be a circular, a square, or an elliptical shape. In this embodiment, the cross-section of the guide column 1112 is a circular shape. Based on the fitting between the guide column 1112 and the guide hole 1113, the connection between the wheel body 112 and the connection body 111 becomes reliable. Referring to FIG. 4 and FIG. 6, optionally, the slidable end of the positioning member 22 engages with the locking member 21 through the positioning grooves 212, so as to realize the reverse rotation limitation of the connection member 11.

In an embodiment, each of the ratchet teeth 211 is arranged obliquely, and an inclination direction of each of the ratchet teeth 211 is opposite to the predetermined direction. It can be understood that when the predetermined direction of rotation of the connection member 11 is clockwise, the free ends of the ratchet teeth 211 are obliquely arranged towards the counterclockwise direction.

Referring to FIG. 4 and FIG. 6, optionally, a tooth surface of each of the ratchet teeth 211 is configured as a convex arc surface 213. When the connection member 11 rotates upward, the convex arc surfaces 213 of the ratchet teeth 211 push the positioning member 22 outwards. After the connection member 11 is rotated in place, the slidable end of the positioning member 22 resets upwards and abuts against a convex surface 213 of a next ratchet tooth 211, in this way, the rotation of the connection member 11 is reversely restricted.

Referring to FIG. 4 and FIG. 6, optionally, an angle between a straight line, which passes through an abutment point of the positioning member 22 and a rotation center of the connection member 11, and the axial direction of the positioning member 22 is between 100 and 120 degrees, optional, in this embodiment, an included angle is 110 degrees.

Optionally, in this embodiment, the fitting between the locking member 21 and the positioning member 22 is similar to a ratchet mechanism.

Referring to FIG. 4 and FIG. 6, in an embodiment, the positioning member 22 comprises: a tongue 221 fitting with the locking member 21, and a reset member 222 having an elastic restoration. The tongue 221 is slidably arranged relative to the locking member 21 and in connection with one end of the reset member 222, and the other end of the reset member 222 is fixedly arranged. Optionally, when the connection member 11 is rotated upwards, the convex arc surfaces 213 of the ratchet teeth 211 push the tongue 221 outward, and the tongue 221 compresses the reset member 222 and elastically deforms the reset member 222. After the connection member 11 is rotated in place, the reset member 222 drives the tongue 221 to slide towards the locking member 21 and until being locked into another positioning groove 212 under the action of the elastic restoring force.

Referring to FIG. 4 and FIG. 6, optionally, the tongue 221 is provided with a guide surface which is adapted to the convex arc surface 213 of the ratchet tooth 211, and the guide surface is configured as a concave arc surface, which facilitates the convex arc surface 213 of a corresponding ratchet tooth 211 to disengage outwards from the tongue 221, and when the tongue 221 is locked by the locking member 21, the guide surface may partially wrap the convex arc surface 213 of a corresponding ratchet teeth 211 to improve the engagement stability.

In an embodiment, the adjusting device 100 further includes an unlocking structure 40, and the unlocking structure 40 includes a pull cord 43, one end of the pull cord 43 is connected to the tongue 221, and the other end of the pull cord 43 is configured to be manipulated manually. By manually pulling the pull cord 43, the tongue 221 is disengaged from the positioning groove 212, and then the downward rotation of the connection member 11 is released, that is, the connection member 11 can freely rotate in two opposite directions.

Referring to FIG. 4 and FIG. 6, in an embodiment, the adjusting device 100 further includes a cowl casing 30 having an accommodation chamber. Optionally, a space in the cowl casing 30 is V-shaped. An avoidance hole 2214 in communication with the accommodation chamber is defined in surface of the cowl casing 30. One end of the connection member 11 is inserted into the accommodation chamber via the avoidance hole 2214 and is rotatably connected to a wall of the accommodation chamber. The positioning structure 20 and the pull cord 43 are both located in the accommodation chamber.

In an embodiment, the wheel body 112 is located in the accommodation chamber and is rotatably connected with the cowl casing 30.

Optionally, the rotating structure 10 further includes a rotating shaft 12 arranged in the accommodation chamber and two ends of the rotating shaft 12 are respectively in connection with walls at two sides of the accommodation chamber. The connection member 11 defines therein a rotation hole, by fitting the rotation hole and the rotating shaft 12, the connection member 11 is rotatably connected to the cowl casing 30.

Optionally, during use, the cowl casing 30 abuts against a shoulder of the human body, and the positioning member 22 is located below the positioning axis.

Figure 7:
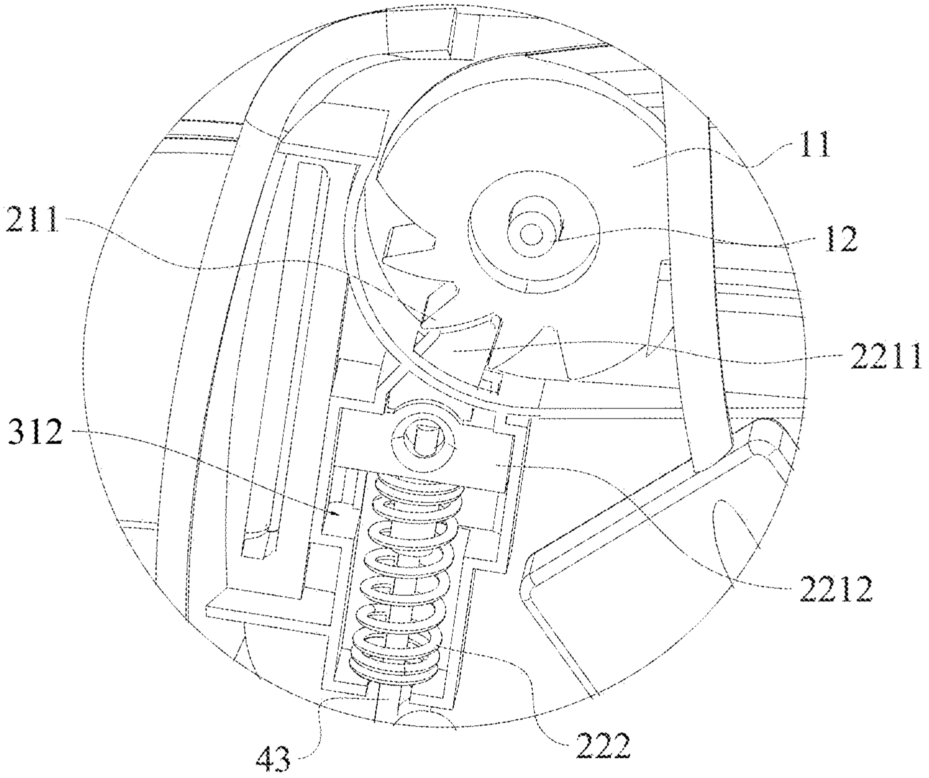
FIG. 7 is a partial enlarged view of Part B taken from FIG. 6.

Referring to FIG. 7, in an embodiment, a guide slot 312 is arranged in the accommodation chamber. One end of the guide slot 312 extends to a connection end of the connection member 11, and the reset member 222 is arranged on the other end of the guide slot 312. The tongue 221 includes: a tongue tip 2211 matching with the locking member 21, a guide block 2212 connected with the tongue tip 2211, and a positioning column 2213 connected with the guide block 2212 and the reset member 222. The pull cord 43 is connected to the positioning column 2213.

In an embodiment, an end of the guide block 2212 abutting against the reset member 222 defines therein a limiting groove 2215, the positioning column 2213 is connected to a bottom of the limiting groove 2215. The reset member 222 is a tube spring, the tube spring is sleeved outside the positioning column 2213. One end of the tube spring abuts against the bottom of the limiting groove 2215, and the other end of the tube spring abuts against an inner wall of the guide slot 312.

It can be understood that the positioning column is inserted into the tube spring, and the tube spring is sleeved outside the positioning column, so that during the elastic deformation process of the tube spring, the tube spring can slide along an axial direction of the positioning column and undergo compression deformation or tensile deformation, making the tube spring remain stable.

Optionally, one end of the tube spring is accommodated in the limiting groove. Based on the cooperation of the limiting groove 2215 and the tube spring, the stability of the tube spring during elastic deformation is improved.

In an embodiment, an inner wall of the guide slot 312 defines therein an avoidance groove 313, and one end of the positioning column 2213 is protruded out of the guide slot 312 via the avoidance groove 313 and connected with the pull cord 43.

Optionally, the tube spring abuts against an opening edge of the avoidance groove 313, and the avoidance groove 313 can also guide the reciprocating sliding of the positioning column 2213.

It can be understood that, when the external force is exerted on the pull cord, the positioning column is pulled by the pull cord to slide toward the avoidance groove, and meanwhile the inner wall of the limit groove compresses the tube spring, and the avoidance groove guides the sliding of the positioning column. After the external force is removed from the pull cord, the tube spring drives the positioning column and the guide block to reset under the action of the elastic restoring force.

Optionally, a guide surface is opened on the tongue tip 2211.

Optionally, the guide slot 312 is arranged along a sliding direction of the tongue 221 and restricts the movement of the tongue 221 laterally.

Optionally, two ends of the guide block 2212 respectively slide against two sidewalls of the guide slot 312, so as to guide the tongue tip 2211 to slide smoothly.

Referring to FIG. 4 and FIG. 6, in an embodiment, two rotating structures 10 are provided. The two rotating structures 10 are respectively located at two ends of the cowl casing 30; the positioning structures 20 and the rotating structures 10 have equivalent numbers and are arranged one-to-one correspondence, the pull cord 43 is arranged along an inner wall of the accommodation chamber, and two ends of the pull cord 43 are respectively connected to two tongues 221.

Figure 5:
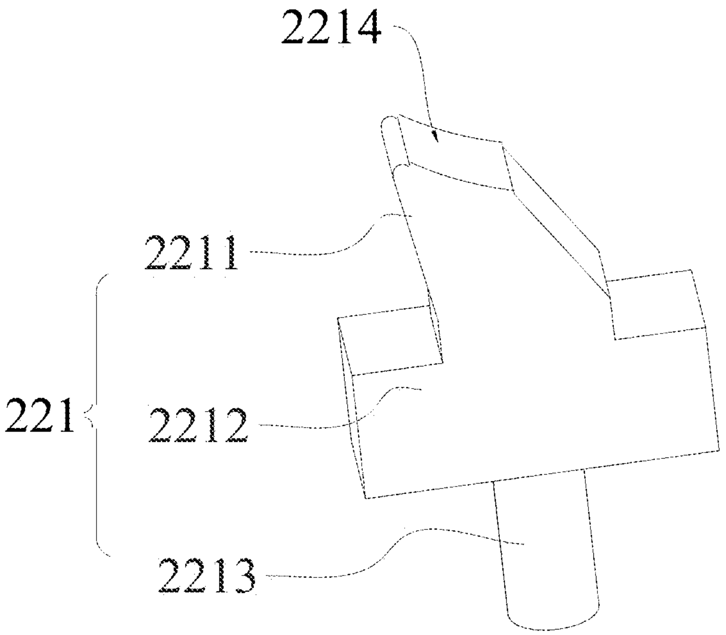
FIG. 5 is a perspective structural schematic diagram of a tongue of FIG. 2.

Referring to FIG. 5 and FIG. 7, optionally, the mandibular support 101 is also arranged in a V-shaped structure, and the two rotating structures 10 are respectively located at two ends of the cowl casing 30, that is, the two ends of the mandibular support 101.

Optionally, a force is exerted at a middle position of the pull cord 43, so that the two ends of the pull cord synchronously pull the tongues 221 away from the locking members 21, so that the two tongues 221 synchronously contact and restrict the two connection members 11, respectively.

Referring to FIG. 5 and FIG. 7, in an embodiment, the cowl casing 30 further defines therein an unlocking hole 311 communicating with the accommodation chamber, and the unlocking structure 40 further includes: an unlocking button 41 located in the unlocking hole 311 and having one end of the unlocking button 41 be connected to the pull cord 43, and rollers 44 which are arranged in the accommodation chamber and configured to guide the pull cord 43 to shrink. Optionally, multiple rollers 44 are provided, and the wheel surfaces of each roller 44 abut against the pull cord 43, and are configured to guide the pull cord 43 to move. An inner wall of the accommodation chamber defines therein sliding grooves along the arrangement position of the pull cord 43, and the pull cord 43 is at least partially accommodated in the sliding grooves along a radial direction thereof, so that the pull cord 43 is pulled smoothly.

Figure 9:
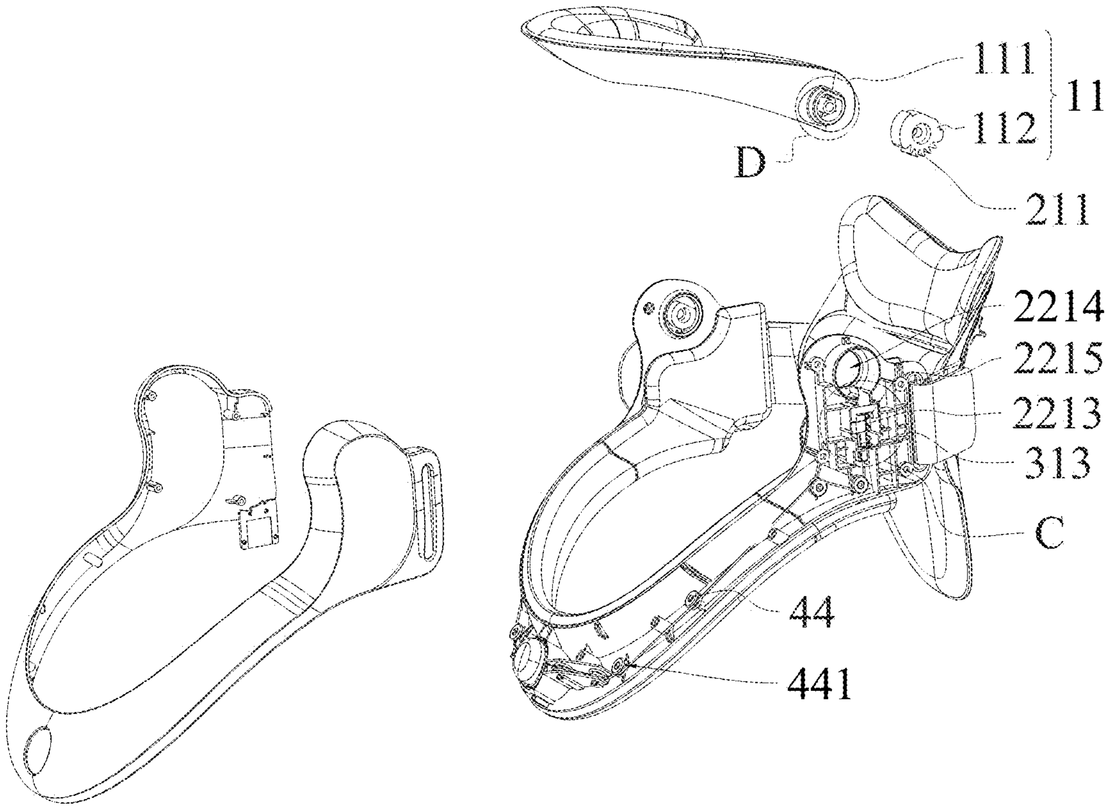
FIG. 9 is an exploded schematic diagram of the adjusting device of FIG. 8.

Referring to FIG. 9, in an embodiment, a roller surface of each of the rollers 44 defines a positioning circular groove 441, and the pull cord 43 is partially accommodated in the positioning circular groove 441.

Referring to FIG. 9, it can be understood that, by accommodating part of the pull cord 43 in the positioning circular grooves 441, the rollers 44 can guide the pull cord 43 to slide reciprocatedly under the cooperation of the positioning circular grooves 441, and during the reciprocated pulling process of the pull cord 43, the pull cord 43 isn't released from the guiding of the rollers, thereby improving the stability and reliability of the slide of the pull cord 43. Referring to FIG. 5 and FIG. 7, optionally, the unlocking structure 40 further includes a return spring 42 located in the accommodation chamber, one end of the return spring 42 abuts against the unlock button 41, and the other end of the return spring 42 is connected to the inner wall of the accommodation chamber.

Referring to FIG. 9, when the release button 41 pulls the pull cord 43, the return spring 42 is simultaneously compressed, and after the external force is removed from the release button 41, the return spring 42 drives the release button 41 to reset.

Optionally, the cowl casing 30 includes a front half casing 31 and a rear half casing 32, the front half casing 31 and the rear half casing 32 are enclosed to form the cowl casing 30.

Referring to FIG. 5 and FIG. 7, the present application also proposes an adjustable cervical spine fixator, which includes an adjusting device 100, the specific structure of which can be referred to the above-mentioned embodiment, since this adjustable cervical spine fixator adopts all the technical solutions of all the above-mentioned embodiments, the adjustable cervical spine fixator also have all the beneficial effects brought by the technical solutions of the above-mentioned embodiments, which will not be repeated here.

When the adjustable cervical spine fixator requires to raise a height of the mandibular support, an external force directly drives the mandibular support to rotate upwards, and the locking member pushes the slidable end of the positioning member to slide outward; and after the external force is removed, the slidable end of the positioning member resets and engages with the locking member, and the locking member reversely engages with the slidable end of the positioning member, so as to realize the positioning of the mandibular support. The operation process is simple and efficient.

Optionally, the adjustable cervical spine fixator further includes an airbag cushion 103 arranged behind the cowl casing 30 and an airbag 102 located at a middle of the cowl casing 30. An air pipe 106 and an air release valve 105 connected to the air pipe 106 are arranged in the accommodation chamber.

The airbag cushion 103 and the airbag 102 can be inflated through the air pipe 106, and an amount of inflation is determined according to a size of the user's neck.

It can be understood that the adjusting device 100 is configured to adjust the height of the mandibular support 101, so as to adapt to different users with different neck lengths.

The above are only optional embodiments of the present application, which are not intended to limit the present application. Various modifications and variations of the present application are possible for those skilled in the art. Any modification, equivalent replacement, improvement, etc. made within the spirit and principle of the present application shall be included within the scope of the claims of the present application.

What is claimed is:

1. An adjusting device, configured to adjust a position of a target, and comprising:

- a rotating structure, comprising a connection member, wherein one end of the connection member is connected with the target and another end of the connection member is rotatable; and
- a positioning structure, comprising a locking member and a positioning member matching with the locking member; wherein the locking member is arranged at a rotatable end of the connection member along a rotation direction of the connection member, one end of the positioning member is slidably arranged relative to the locking member, and another end of the positioning member is fixedly arranged;

wherein the connection member is configured to rotate in a predetermined direction, and drive a slidable end of the positioning member to slide in a direction away from the locking member; and the slidable end of the positioning member is configured to reset and engage with the locking member and reversely restrict rotation of the connection member, after the connection member is rotated in place;

a cowl casing having an accommodation chamber, wherein an avoidance hole in communication with the accommodation chamber is defined in surface of the cowl casing; one end of the connection member is inserted into the accommodation chamber via the avoidance hole and is rotatably connected to a wall of the accommodation chamber; and an unlocking structure, the unlocking structure comprising a pull cord, the positioning structure and the pull cord are both located in the accommodation chamber.

2. The adjusting device according to claim 1, wherein the locking member comprises ratchet teeth, and the ratchet teeth are arranged at intervals along a peripheral side of the connection member, and a positioning groove is formed between any two adjacent ratchet teeth, and one end of the positioning member is engaged into one positioning groove.

3. The adjusting device according to claim 2, wherein the connection member comprises a connection body and a wheel body connected to the connection body; and the ratchet teeth are arranged at a peripheral side of the wheel body.

4. The adjusting device according to claim 3, wherein the connection body defines therein a connection hole, a cross-section of the connection hole has a non-circular shape, and the wheel body protrudes towards the connection hole to form a connection portion.

5. The adjusting device according to claim 4, wherein a guide column is arranged in the connection hole, and a guide hole matching with the guide column is defined in a position of the connection portion corresponding to the guide column; and one end of the guide column is plugged into the guide hole.

6. The adjusting device according to claim 5, wherein the positioning member comprises: a tongue fitting with the locking member, and a reset member having an elastic restoration; and the tongue is slidably arranged relative to the locking member and in connection with one end of the reset member, and another end of the reset member is fixedly arranged.

7. The adjusting device according to claim 2, wherein each of the ratchet teeth is arranged obliquely, and an inclination direction of each of the ratchet teeth is opposite to the predetermined direction.

8. The adjusting device according to claim 1, wherein the positioning member comprises: a tongue fitting with the locking member, and a reset member having an elastic restoration; and the tongue is slidably arranged relative to the locking member and in connection with one end of the reset member, and another end of the reset member is fixedly arranged.

9. The adjusting device according to claim 8, wherein one end of the pull cord is connected to the tongue.

10. The adjusting device according to claim 9, wherein a guide slot is arranged in the accommodation chamber; one end of the guide slot extends to a connection end of the connection member, and the reset member is arranged on another end of the guide slot;

the tongue comprises: a tongue tip matching with the locking member, a guide block connected with the tongue tip, and a positioning column connected with the guide block and the reset member; and the pull cord is connected to the positioning column.

11. The adjusting device according to claim 10, wherein an end of the guide block abutting against the reset member defines therein a limiting groove, the positioning column is connected to a bottom of the limiting groove;

the reset member is a tube spring, the tube spring is sleeved outside the positioning column; and one end of the tube spring abuts against the bottom of the limiting groove, and another end of the tube spring abuts against an inner wall of the guide slot.

12. The adjusting device according to claim 10, wherein the inner wall of the guide slot defines therein an avoidance groove, and one end of the positioning column is protruded out of the guide slot via the avoidance groove and connected with the pull cord.

13. The adjusting device according to claim 10, wherein the cowl casing further defines therein an unlocking hole communicating with the accommodation chamber; and the unlocking structure further comprises:

an unlocking button, which is located in the unlocking hole and has one end of the unlocking button connected to the pull cord, and rollers, which are arranged in the accommodation chamber and configured to guide the pull cord to shrink.

14. The adjusting device according to claim 13, wherein a roller surface of each of the rollers defines a positioning circular groove, and the pull cord is partially accommodated in the positioning circular groove.

15. The adjusting device according to claim 1, wherein the rotating structure is one of two rotating structures;

the two rotating structures are respectively located at two ends of the cowl casing;

a number of positioning structures is equivalent to that of the rotating structures, and the positioning structures and the rotating structures are arranged one-to-one correspondence; and the pull cord is arranged along an inner wall of the accommodation chamber, and two ends of the pull cord are respectively connected to two tongues.

16. An adjustable cervical spine fixator, comprising an adjusting device, configured to adjust a position of a target, and comprising:

a rotating structure, comprising a connection member, wherein one end of the connection member is connected with the target and another end of the connection member is rotatable; and a positioning structure, comprising a locking member and a positioning member matching with the locking member; wherein the locking member is arranged at a rotatable end of the connection member along a rotation direction of the connection member, one end of the positioning member is slidably arranged relative to the locking member, and another end of the positioning member is fixedly arranged;

wherein the connection member is configured to rotate in a predetermined direction, and drive a slidable end of the positioning member to slide in a direction away from the locking member; and the slidable end of the positioning member is configured to reset and engage with the locking member and reversely restrict rotation of the connection member, after the connection member is rotated in place;

a cowl casing having an accommodation chamber, wherein an avoidance hole in communication with the accommodation chamber is defined in surface of the cowl casing; one end of the connection member is inserted into the accommodation chamber via the avoidance hole and is rotatably connected to a wall of the accommodation chamber; and an unlocking structure, the unlocking structure comprising a pull cord, the positioning structure and the pull cord are both located in the accommodation chamber.

17. The adjustable cervical spine fixator according to claim 16, wherein the locking member comprises ratchet teeth, and the ratchet teeth are arranged at intervals along a peripheral side of the connection member, and a positioning groove is formed between any two adjacent ratchet teeth, and one end of the positioning member is engaged into one positioning groove.

18. The adjustable cervical spine fixator according to claim 17, wherein the connection member comprises a connection body and a wheel body connected to the connection body; and the ratchet teeth are arranged at a peripheral side of the wheel body.

19. The adjustable cervical spine fixator according to claim 18, wherein the connection body defines therein a connection hole, a cross-section of the connection hole has a non-circular shape, and the wheel body protrudes towards the connection hole to form a connection portion.

* * * * *